United States Patent [19]

Hellstrom et al.

[11] Patent Number: 5,171,665

[45] Date of Patent: Dec. 15, 1992

[54] MONOCLONAL ANTIBODY TO NOVEL ANTIGEN ASSOCIATED WITH HUMAN TUMORS

[75] Inventors: Ingegerd Hellstrom; Karl E. Hellstrom, both of Seattle; Hans Marquardt, Mercer Island, all of Wash.

[73] Assignee: Oncogen, Seattle, Wash.

[21] Appl. No.: 339,142

[22] Filed: Apr. 17, 1989

[51] Int. Cl.$^5$ .................. G01N 33/574; C12P 21/08; C07K 15/28

[52] U.S. Cl. .................. 435/7.23; 435/7.9; 435/172.2; 435/240.27; 436/548; 436/813; 436/64; 530/387.7; 530/388.8; 530/388.85

[58] Field of Search ............. 435/7.23, 172.2, 240.27, 435/7.9; 436/548, 813, 64; 530/387, 387.7, 388.8, 388.85

[56] References Cited

U.S. PATENT DOCUMENTS

| | | | |
|---|---|---|---|
| 4,474,893 | 10/1984 | Reading | 436/547 |
| 4,507,391 | 3/1985 | Pukel et al. | 436/504 |
| 4,579,827 | 4/1986 | Sakamoto et al. | 436/536 |
| 4,612,282 | 9/1986 | Schlom et al. | 435/68 |
| 4,676,980 | 6/1987 | Segal | 424/85 |
| 4,708,930 | 11/1987 | Kortright et al. | 435/7 |
| 4,713,351 | 12/1987 | Knauf | 436/542 |
| 4,713,352 | 12/1987 | Bander et al. | 436/548 X |
| 4,737,579 | 4/1988 | Hellstrom et al. | 530/387 |
| 4,753,894 | 6/1988 | Frankel et al. | 436/548 |
| 4,906,562 | 3/1990 | Hellstrom et al. | 435/7 |

FOREIGN PATENT DOCUMENTS

| | | |
|---|---|---|
| 0323802 | 7/1989 | European Pat. Off. . |
| 0338846 | 10/1989 | European Pat. Off. . |
| 2186885A | 8/1987 | United Kingdom . |

OTHER PUBLICATIONS

Papsidero, "Recent Progress in the Immunological Monitoring of Carcinomas Using Monoclonal Antibodies" *Sem. in Surg. Onc.* 1:171-181 (1985).

Schlom and Weeks, "Potential Clinical Utility of Monoclonal Antibodies in the Management of Human Carcinomas" Important Adv. Oncol., 170-92 (1985).

Allum et al., "Monoclonal Antibodies in the Diagnosis and Treatment of Malignant Conditions" *Surg. Ann.*, 18:41-64 (1986).

Houghton and Scheinberg, "Monoclonal Antibodies: Potentail Applications to the Treatment of Cancer" Semin. Oncol., 13(2):165-79 (1986).

Hellstrom et al., "Monoclonal Mouse Antibodies Raised Against Human Lung Carcinoma", Cancer Res., 46:3917 (1986).

Fink and Clarke, "Monoclonal Antibodies as Diagnostic Reagents for the Identification and Characterization of Human Tumor Antigens" Prog. Clin. Pathol. 9:121—33 (1984).

Johnston, "Applications of Monoclonal Antibodies in Clinical Cytology as Exemplified by Studies with Monoclonal Antibody B72.3", Acta. Cytol., 1(5):537-56 (1987).

Young et al., "Production of monoclonal antibodies specific for two distinct steric portions of the glycolipid anglio-N-tiosylceramide (Asialo GM$_2$) *J. Exp. Med.*, 150:1008-1019 (1979).

Kniep et al., "Gangliotriaosylceramide (Asialo GM$_2$) A glycosphingolipid marker for cell lines derived from patients with Hodgkin's disease", *J. Immunol.*, 131:1591-1594 (1983).

Rosen et al., "Analysis of Human Small Cell Lung Cancer Differentiation Antigens Using a Panel of Rat Monoclonal Antibodies" Cancer Res. 44:1052-2061 (1984).

Varki et al., "Antigens associated with a Human Lung Adenocarcinoma Defined by Monoclonal Antibodies" Cancer Res., 44:681-687 (1984).

Hellstrom et al., "Antitumor effects of L6, an IgG2a antibody that reacts with most human carcinomas", *Proc. Nat. Acad. Sci USA*, 83:7059-7063 (1986).

Kohler and Milstein, "Continuous cultures of fused cells secreting antibody of predefined specificity" *Nature* (London) 256:495 (1975).

Brown et al., "Structural Characterization of Human Melanoma-Associated Antigen p. 97 with Monoclonal Antibodies", *J. Immunol.*, 127(2):539-46 (1981).

Brown et al., "Protein Antigens of Normal and Malignant Human Cells Identified by Immunoprecipitation with Monoclonal Antibodies", *J. Biol. Chem.*, 255:4980-83 (1980).

Yeh et al., "Cell surface antigens of human melanoma identified by monoclonal antibody" *Proc. Natl. Acad. Sci. USA* 76(6):2927-31 (1979).

(List continued on next page.)

*Primary Examiner*—Esther L. Kepplinger
*Assistant Examiner*—Toni R. Scheiner
*Attorney, Agent, or Firm*—Saralynn Mandel; Sheldon & Mak

[57] ABSTRACT

The present invention is concerned with a novel monoclonal antibody which binds strongly to a protein antigen associated with human tumors, including carcinomas of the colon and lung. The antibody binds to normal human cells to a much lesser degree than to tumor cells. The antibody finds use both in diagnostic methods such as the detection of malignant cells associated with tumors and in therapeutic methods for treatment of humans with tumors. Also disclosed is a novel 66,000 dalton glycoprotein antigen found on the cell surface of human tumor cells. The amino terminal amino acid sequence of this antigen is:

```
1           5             10
X—E—L—T—I—L—H—T—N—D—V—H—S—R—
                            15         20
                            L—E—Q—T—S—X
``` in which X represents an unidentified amino acid.

24 Claims, No Drawings

OTHER PUBLICATIONS

Yeh et al., "A cell-surface antigen which is present in the ganglioside fraction and shared by human melanomas", *Int. J. Cancer*, 29:269-75 (1982).

Zola et al., in "Monoclonal Hybridoma Antibodies: Techniques and Applications", Hurrell (Ed.), pp. 51-52 (CRC Press, 1982).

Cole et al., "Human monoclonal antibodies", *Mol. Cell. Biol.*, 62:109-120 (1984).

Shawler et al., "Human immune response to multiple injections of murine monoclonal IgG1", *J. Immunol.*, 135:1530-35 (1985).

Oi, "Chimeric Antibodies", *Biotechniques* 4(3):214-21 (1986).

Liu et al., "Chimeric mouse-human IgG1 Antibody that can mediate lysis of cancer cells", *Proc. Natl. Acad. Sci USA*, 84:3439-3443 (1987).

Borrabaeck et al., "Human monoclonal antibodies produced by primary in vitro immunization of peripheral blood lymphocytes", *Proc. Natl. Acad. Sci. USA*, 85:3995-99 (1988).

Hellstrom et al., "Covalently Modified Antigens and Antibodies in Diagnosis and Therapy", Quash/Rodwell (Eds.), pp. 24-28 Macel Dekker, Inc., (1989).

Rouseaux et al., "Optimal Conditions for the Preparation of Proteolytic Fragments from Monoclonal IgG of Different Rat IgG Subclasses" in *Methods Enzymol.*, 121:663-69 (Academic Press, (1986).

Bagshawe, "Tumor markers — Where do we go from here?", *Br. J. Cancer*, 48:167-75 (1983).

Thammana et al., "Immunoglobulin Heavy Chain Class Switch from IgM to IgG in a Hybridoma", *Eur. J. Immunol.*, 13:614 (1983).

Spira et al., "The Identification of Monoclonal Class Switch Variants by Subselection and ELISA Assay", *J. Immunol. Meth.*, 74:307-15 (1984).

Neuberger et al., "Recombinant antibodies possessing novel effector functions" *Nature*, 312:604-608 (1984).

Nepom et al., "Anti-idiotypic antibodies and the induction of specific tumor immunity", in Cancer and Metastasis Reviews", 6:487-501 (1987).

Lee et al., "Monoclonal antiidiotypic antibodies related to a murine oncofetal bladder tumor antigen induce specific cell-mediated tumor immunity", *Proc. Natl. Acad. Sci. USA*, 82:6286-69 (1985).

Hakamori, "Tumor-Associated Carbohydrate Antigens", *Ann. Rev. Immunol.*, 2:103-26 (1984).

Brown et al., "Human melanoma-associated antigen p97 is structurally and functionally related to transferrin", *Nature*, 296:171-173 (1982).

Rose et al., "Primary structure of the human melanoma-associated antigen p97 (melanomatransferrin) deduced from the mRNA sequence", *Proc. Natl. Acad. Sci USA* 83:1261-1265 (1986).

Ciocca et al., "Immunohistochemical Techniques Using Monoclonal Antibodies" *Meth. Enzymol.*, 121-562-79 (1986).

Kimball (Ed.), *Introduction to Immunology*, (2nd Ed.), pp. 113-117 (Macmillan Publ. co.) (1986).

Uotila et al., "Two-site sandwich enzyme immunoassay with monoclonal antibodies to human alpha-fetoprotein" *J. Immunol. Methods*, 42:11 (1981).

Sikora et al., (Eds.), *Monoclonal Antibodies*, pp. 32-52 (Blackwell Scientific Publ., 1984).

Wensel and Meares, "'Bifunctional' Chelating Agents for Binding Metal Ions to Proteins" *Radioimmunoimaging and Radioimmunotherapy*, Esevier, N.Y. (1983).

Colcher et al., "Use of Monoclonal Antibodies as Radiopharmaceuticals for the Localization of Human Carcinoma Xenografts in Athymic Mice", *Meth. Enzymol.*, 121:802-16 (1986).

Bradwell et al., "Developments in Antibody Imaging", in *Monoclonal Antibodies for Cancer Detection and Therapy*, Baldwin et al., (Eds.), pp. 65-85, Academ. Press (1985).

Arnon et al., "Monoclonal Antibodies for Immunotargeting of Drugs in Cancer Therapy" in Monoclonal Antibodies and Cancer Therapy, Reisfeld et al., (Eds.), pp. 243-256 (Alan R. Liss, Inc. 1985).

Hellstrom et al., "Antibodies for Drug Delivery" in *Controlled Drug Delivery* (2nd Ed.), Robinson et al., (Eds.), (Marcel Dekker Inc., 1987).

Thorpe, "Antibody Carriers of Cytotoxic Agents in Cancer Therapy: A review" in Monoclonal Antibodies '84: Biological and Clinical Applications, Pinchera et al., Eds., pp. 475-506 (1985).

Thorpe et al., "The Preparation and Cytotoxic Properties of Antibody—Toxin Conjugates" *Immunol. Rev.*, 62:119-58 (1982).

Order, "Analysis, Results and Future Prospective of the Therapeutic Use of Radiolabeled Antibody in Cancer Therapy", in *Monoclonal Antibodies for Cancer Detection and Therapy* Baldwin (Eds.) pp. 303-316, Academ. Press (1985).

Senter et al., "Anti-tumor effects of antibody-alkaline phosphatase conjugates in combination with etoposide phosphate", Proc. Natl. Acad. Sci. USA, 85:4842-4846 (1988).

Ramsey et al., "Bone Marrow Purigng Using Monoclonal Antibodies", *J. Clinical Immunol.*, 8(2):81-88 (1988).

Estin et al., "Recombinant vaccinia virus vaccine against the human melanoma antigen p97 for use in immunotherapy" *Proc. Natl. Acad Sci USA*, 85:1052 (1988).

Hu et al., "Characterization of a recombinant vaccinia virus expressing human melanoma-associated antigen p97", *J. Virol.*, 62:176-180 (1988).

Bradford, "A rapid and sensitive method for the quantitation of microgram quantities of protein utilizing the principle of protein-dye binding" *Analytic Biochem.*, 72:248-254 (1976).

Douillard and Hoffman, "Enzyme-Linked Immunosorbent Assay for Screening Monoclonal Antibody Production Using Enzyme-Labeled Second Antibody" *Meth. Enzymol.*, 92:168-74 (1983).

Ey et al., "Isolation of pure IgG1, IgG2a and IgG2b immunoglobulins from mouse serum using protein A-Sepharose *Immunochemistry*, 15:429-436 (1978).

Sternberger, "The Unlabeled Antibody Perioxidas-Antiperoxidase (PAP) Method" in Immunochemistry, pp. 104-169 (John Wiley & Sons, N.Y., 1979).

(List continued on next page.)

OTHER PUBLICATIONS

Garrigues et al., "Detection of a Human Melanoma-Associated Antigen, p97, in Histological Sections of Primary Human Melanomas", *Int. J. Cancer*, 29:511-15 (1982).

Hellstrom et al., "Monoclonal Antibodies to two Determinants of Melanoma-Antigen p97 Act Synergistically in Complement-Dependent Cytotoxicity", *J. Immunol.*, 127:157-60 (1981).

Matsudaira, "Sequence from picomole quantities of proteins electroblotted onto polyvinyliden difluoride membranes" *J. Biol. Chem.*, 262:10035-10038 (1987).

Towbin et al., "Electrophoretic transfer of proteins from polyacrylamide gels to nitrocellulose sheets: procedure and some applications", *Proc. Natl. Acad. Sci. USA*, 76:4350-4354 (1979).

Vitetta et al., "Cell surface immunoglobulin", *J. Exp. Med.*, 134:242-264 (1971).

La Vie et al., "Evaluation of L6, an anticarcinoma murine monoclonal antibody, in tumor-bearing nude mice", *J. Surg. Res.* (Biological Abstracts, vol. 88(9), Nov. 1989).

Gottlinger et al., "Biochemical characterization and tissue distribution of the cora antigen, a cell surface glycoprotein differentially expressed on Malignant and benign gastrointestinal epithelia", *Cancer Res.*, 28(15):2198-2203 (1988).

Ho et al., "Tissue distribution, immunochemical characterization, and biosynthesis of 47D10, a tumor-associates surface glycoprotein" *Cancer Res.*, 47:241-250 (1987).

Holmgren et al., "Detection by monoclonal antibody of carbohydrates antigen CA 50 in serum of patients with carcinoma", *Br. Med. Journal*, 288:1479-1482 (1984).

Pak et al., "Identification and isolation of a common tumor-associated molecule using monoclonal antibody", *Molecular Immunology*, 20(12):1369-1377 (1983).

Carrasquillo et al., "Diagnosis of and therapy for solid tumors with radiolabeled antibodies and immune fragments", *Biological Abstracts*, vol. 78(1), (Cancer Treat Resp., 68(1):317-328 (1984)).

Hellstrom et al., "Antibody-mediated killing of —uman tumor cells by attached effector cells"*Cancer Res.*, 48:624-627 (1988).

Rowland et al., "Antitumor properties of vindesine-monoclonal antibody conjugates" (*Biological Abstracts*, vol. 82(10), Nov. 1986).

Pak et al. *Molecular Immunol.* 20(12):1369-1377, 1983.
Holmgren et al. *British Med. J.* 288:1479-1482, 1984.
Hellström et al. *Cancer Res.* 46:3917-3923, 1986.
Ho et al. *Cancer Res.* 47:241-250, 1987.
Göttlinger et al. *Cancer Res.* 48:2198-2203, 1988.

MONOCLONAL ANTIBODY TO NOVEL ANTIGEN ASSOCIATED WITH HUMAN TUMORS

FIELD OF THE INVENTION

The present invention relates to a novel monoclonal antibody and a novel antigen, and to methods for production and use of such novel monoclonal antibody reactive with human carcinoma cells. More specifically, the monoclonal antibody of this invention is reactive with the novel cell surface antigen which is associated with a variety of human tumors including carcinomas of the colon and lung.

The monoclonal antibody of this invention is suitable for both in vivo and in vitro clinical diagnostic purposes, such as the detection of malignant carcinomas. Additionally the antibody of the present invention is suited for therapeutic uses, for example to react with tumor cells, and in conjugates as a target-selective carrier of various agents which have anti-tumor effects including, but not limited to: chemotherapeutic drugs, toxins, immunological response modifiers, and radioisotopes. The antigen of the invention is also useful for therapeutic and diagnostic purposes.

BACKGROUND OF THE INVENTION

Carcinomas cause millions of deaths annually. For example, lung carcinomas are responsible for the majority of deaths from cancer among men and are overtaking breast carcinomas as the most frequent cause of cancer death among women. Most cases of carcinomas are incurable by chemotherapy and radiation therapy unless radically removed in the early stages of the disease. There is thus a great need for methods of diagnosis and therapy of carcinomas of the breast, colon, ovary and lung, as well as for other malignant neoplasms such as melanomas and sarcomas.

Monoclonal antibodies reactive with carcinoma-associated antigens are known (see, e.g., Papsidero, *Semin. Surg. Oncol.*, 1 (4):171–81 (1985); Schlom et al., *Important Adv. Oncol.*, 170–92 (1985); Allum et al., *Surg. Ann.*, 18:41–64 (1986); Houghton et al., *Semin. Oncol.*, 13 (2):165–79 (1986); *Monoclonal Antibodies in Cancer: Advances for Diagnosis and Treatment*, Roth (ed.), Futura Publishing, Mt. Kisco, N.Y. (1986); and *Cancer Diagnosis In Vitro Using Monoclonal Antibodies*, Kupchik (ed.) Marcel Dekker, Inc., New York, (1988)).

Most of the known monoclonal antibodies are reactive with several types of human carcinomas, while a few antibodies react with carcinomas derived from specific organs of the body, e.g., lung, breast, ovary, colon, stomach or pancreas. The glycolipids (see, e.g., Hellstrom et al., *Cancer Research*, 46:3917–23 (1986); and Fink et al., *Prog. Clin. Pathol.*, 9:121–33 (1984)). For example, monoclonal antibodies reactive with glycoprotein antigens on specific types of carcinomas include those described in U.S. Pat. No. 4,737,579 (monoclonal antibodies to non-small cell lung carcinomas); U.S. Pat. No. 4,753,894 (monoclonal antibodies to human breast cancer); U.S. Pat. No. 4,579,827 (monoclonal antibodies to human gastrointestinal cancer); and U.S. Pat. No. 4,713,352 (monoclonal antibodies to human renal carcinoma). Some monoclonal antibodies react with high molecular weight antigens which appear to be mucins. For example, monoclonal antibody B72.3 appears to recognize a tumor-associated oncofetal glycoprotein antigen of greater than 1,000 kd molecular weight that is selectively expressed on a number of different carcinomas. Thus, B72.3 has been shown to react with 84% of breast carcinomas, 94% of colon carcinomas, 100% of ovarian carcinomas and 96% of non-small-cell lung carcinomas (see Johnston, *Acta Cytol.*, 1 (5):537–56 (1987) and U.S. Pat. No. 4,612,282, issued to Schlom et al.). Similarly, monoclonal antibody KC-4 recognizes an approximately 400–500 kd protein antigen expressed on a number of carcinomas, such as colon, prostate, lung and breast carcinoma (See U.S. Pat. No. 4,708,930).

Monoclonal antibodies reactive with glycolipid antigens that are believed to be associated with certain tumor cells have also been disclosed. For example, Young et al., *J. Exp. Med.*, 150:1008–19 (1979) disclose the production of two monoclonal antibodies specific for asialo $GM_2$, a cell surface glycosphingolipid antigen that was established as a marker for BALB/c 3T3 cells transformed by Kirsten murine sarcoma virus. See, also, Kniep et al., *J. Immunol.*, 131 (3):1591–94 (1983) and U.S. Pat. No. 4,507,391 (monoclonal antibody to human melanoma).

In addition, monoclonal antibodies reactive with glycolipid antigens found on specific types of carcinoma cells include those described by Rosen et al., *Cancer Research*, 44:2052–61 (1984) (monoclonal antibodies to human small cell lung cancer); Varki et al., *Cancer Research*, 44:681–87 (1984) (monoclonal antibodies to human adenocarcinomas of the lung, stomach and colon and melanoma); and U.S. Pat. No. 4,579,827 (monoclonal antibodies to human colon adenocarcinoma). See, also, Hellstrom et al., *Proc. Nat'l. Acad. Sci. USA*, 83:7059–63 (1986) which describes the L6 monoclonal antibody that recognizes a carbohydrate antigen expressed on the surface of human non-small cell lung carcinomas, breast carcinomas and colon carcinomas.

Additional monoclonal antibodies exhibiting a reactivity to antigens found on a variety of tumor cells are greatly needed. This is because of the antigenic heterogeneity of most tumors which often necessitates, in diagnosis or therapy, the use of a combination of different monoclonal antibodies directed to the same tumor mass. Furthermore, monoclonal antibodies that display a high degree of reactivity with a wide range of tumors, while showing the absence of or only a very weak reactivity with normal tissues, are not common. Such antibodies would clearly be advantageous.

It is thus apparent that a monoclonal antibody reactive with an antigen expressed at high levels by a variety of tumors may become useful towards an earlier diagnosis of cancers, a better definition of the spread of the cancer, the immunological monitoring of cancer patients, as well as for development of improved methods for therapy of cancers. It is also apparent that monoclonal antibodies to novel cell surface molecules can be used for further definition of such molecules which may be of value for preparing immunogens in the form of cancer vaccines, and which may also have important cellular functions, for example, as receptors of hormones or growth factors or as molecules otherwise involved in intra- and intercellular communication. The antigens may even have enzymatic or growth factor activity by themselves.

SUMMARY OF THE INVENTION

The present invention provides such a monoclonal antibody, Cl, which is specific for a determinant site on a cell surface glycoprotein antigen, the Cl antigen, associated with human tumor cells, particularly cells from lung and colon carcinomas. Thus, the antibody of the invention can be useful for the diagnosis and therapy of tumors expressing the Cl antigen identified by antibody Cl. The Cl antibody of the invention is of the class IgG, and IgG1 subclass, and it shows no significant reactivity with normal human cells.

The antibody of the invention may be used in in vitro diagnostic methods for determining the presence of a malignant condition in human lung tissue and other human tissues. The methods involve examining the tissue for the presence of an antigen having the characteristics of the 66,000 dalton Cl antigen glycoprotein reactive with antibody Cl. For example, the tissue can be contacted with the Cl monoclonal antibody of the invention which defines a determinant site on a cell-associated antigen having the characteristics of the Cl antigen, a functional equivalent or a fragment of this antibody and any interactions of said antibody and antigenic determinants are detected. One such method involves the determination of the presence of carcinoma cells in a specimen suspected of containing such cells. The specimen is contacted with the monoclonal antibody, which is capable of distinguishing such cells from other cell types which may be present in the specimen. The contact is carried out under conditions for binding of the antibody to such cells. After contact, the presence or absence of binding of the antibody to the cells in the specimen is determined. This binding is related to the presence or absence of carcinoma cells in the specimen. Generally, the specimen is contacted with a labeled specific binding partner of the monoclonal antibody. This label is capable of producing a detectable signal. Alternatively, the monoclonal antibody itself may be labeled.

Another diagnostic method involves the in vivo localization of a tumor by administering to a patient a purified antibody or antibody fragment of the present invention labeled with an agent which gives a detectable signal. The localization is then detected using external scintigraphy, emission tomography or radionuclear scanning. This method can also provide better ways to stage cancer patients with respect to the extent of disease and to monitor changes in response to therapy.

The invention also has therapeutic applications, since the Cl antibody and similar antibodies can react with the Cl antigen that is expressed in high concentrations at the tumor cell surface. The monoclonal antibody of the invention may be used to prepare a composition for treating tumors. The composition comprises a therapeutically effective amount of the antibody in association with a pharmaceutically acceptable parenteral vehicle. The antibody of the invention can also be used in immunoconjugates as a carrier of various agents which have an antitumor effect, including, but not restricted to, chemotherapeutic drugs, toxins, immunological response modifiers, and radioisotopes.

The invention also comprises the novel Cl antigen characterized by a molecular weight of about 66,000 daltons and having an amino terminal amino acid sequence:

$$\underset{1}{X}-E-\underset{5}{L}-T-I-L-H-T-N-\underset{10}{D}-V-H-S-R-$$

-continued $$\underset{15}{L}-E-Q-T-S-\underset{20}{X}$$

in which X represents an unidentified amino acid, and equivalents, identified by antibody Cl and the class of antibodies that bind to this antigen.

The invention includes methods for using the purified or cloned Cl antigen as a vaccine to immunize against certain tumors.

DETAILED DESCRIPTION OF INVENTION

In order that the invention herein described may be more fully understood, the following detailed description is set forth.

The present invention concerns a novel monoclonal antibody, designated Cl, which is specifically reactive with an antigen (Cl antigen) localized on human tumor cells, particularly from carcinomas of the lung and colon, methods for producing the Cl monoclonal antibody and diagnostic and therapeutic methods employing the antibody. The Cl antibody reacts with a range of tumors while showing essentially no reactivity with normal human tissues or other types of tumors such as melanomas or lymphomas.

The invention further concerns a novel cell surface glycoprotein antigen, designated Cl antigen, and primarily associated with human tumors of the lung and colon, and methods for using the Cl antigen.

The monoclonal antibody of the invention can be prepared by hybridoma fusion techniques or by techniques that utilize EBV-immortalization technologies.

Hybridoma fusion techniques were first introduced by Kohler and Milstein (see, Kohler and Milstein, *Nature*, 256:495-97 (1975); Brown et al., *J. Immunol.*, 127 (2):539-46 (1981); Brown et al., *J. Biol. Chem.*, 255:4980-83 (1980); Yeh et al., *Proc. Nat'l. Acad. Sci. (USA)*, 76 (6):2927-31 (1976); and Yeh et al., *Int. J. Cancer*, 29:269-75 (1982)).

These techniques involve the injection of an immunogen (e.g., purified antigen or cells or cellular extracts carrying the antigen) into an animal (e.g., a mouse) so as to elicit a desired immune response (i.e., production of antibodies) in that animal. For example, human lung carcinoma cells from pleural effusions, cultured cells from explanted human non-small cell lung carcinomas (NSCLC), or cells from a normal fetal lung or lysates from such cells may be used as the immunogen. In Example I, infra, a membrane preparation from human adenocarcinoma of the colon designated H3059 and cells from the colon carcinoma cell line 3347 are used as the immunogen. The membrane preparation is injected, for example, into a mouse, and after a sufficient time the mouse is sacrificed and somatic antibody-producing lymphocytes are obtained. Antibody-producing cells may be derived from the lymph nodes, spleens and peripheral blood of primed animals. Spleen cells are preferred. Mouse lymphocytes give a higher percentage of stable fusions with the mouse myelomas described below. The use of rat, rabbit and frog somatic cells is also possible. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-

Ag8.653 or Sp2/O-Ag14 myeloma lines. These myeloma lines are available from the American Type Culture Collection (ATCC), Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the antigen that has been used for immunization. Positive clones can then be subcloned under limiting dilution conditions, and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Zola et al., in *Monoclonal Hybridoma Antibodies: Techniques and Applications*, Hurell (ed.) pp. 51-52 (CRC Press 1982)). Hybridomas produced according to these methods can be propagated in vitro or in vivo (in ascites fluid) using techniques known in the art (See, generally, Fink et al., supra, at page 123, FIG. 6-1).

Generally, the individual cell line may be propagated in vitro, for example in laboratory culture vessels, and the culture medium containing high concentrations of a single specific monoclonal antibody can be harvested by decantation, filtration or centrifugation. Alternatively, the yield of monoclonal antibody can be enhanced by injecting a sample of the hybridoma into a histocompatible animal of the type used to provide the somatic and myeloma cells for the original fusion. Tumors secreting the specific monoclonal antibody produced by the fused cell hybrid develop in the injected animal. The body fluids of the animal, such as ascites fluid or serum, provide monoclonal antibodies in high concentrations. As discussed by Cole et al., supra, when human hybridomas or EBV-hybridomas are used, it is necessary to avoid rejection of the xenograft injected into animals such as mice. Immunodeficient or nude mice may be used or the hybridoma may be passaged first into irradiated nude mice as a solid subcutaneous tumor, cultured in vitro and then injected intraperitoneally into pristane primed, irradiated nude mice which develop ascites tumors secreting large amounts of specific human monoclonal antibodies (See Cole et al., supra).

For certain therapeutic applications chimeric (mouse-human) or human monoclonal antibodies may be preferable to murine antibodies because patients treated with mouse antibodies generate human antimouse antibodies. (Shawler et al., *J. Immunol.*, 135:1530-35 (1985)). Chimeric mouse-human monoclonal antibodies reactive with the Cl antigen can be produced, for example, by techniques recently developed for the production of chimeric antibodies (Oi et al., *Biotechnologies*, 4(3):214-221 (1986); Liu et al., *Proc. Nat'l. Acad. Sci. (USA)*, 84:3439-43 (1987)). Accordingly, genes coding for the constant regions of the murine Cl antibody molecule are substituted with human genes coding for the constant regions of an antibody with appropriate biological activity (such as the ability to activate human complement and mediate ADCC). Novel antibodies of mouse or human origin, can also be made to the Cl antigen having the appropriate biological functions. For example, human monoclonal antibodies may be made by using the antigen, e.g., the Cl antigen of the invention, to sensitize human lymphocytes to the antigen in vitro followed by EBV-transformation or hybridization of the antigen-sensitized lymphocytes with mouse or human lymphocytes as described by Borrebaeck et al. (*Proc. Nat'l. Acad. Sci. (USA)*, 85:3995-99 (1988)).

According to a preferred embodiment, the antibody of this invention, designated Cl, was produced via hybridoma techniques using membranes from colon adenocarcinoma effusion cells and cells from a colon carcinoma cell line 3347 as the immunogen as described in Example I, infra. The Cl hybridoma, producing the Cl antibody, has been deposited with the American Type Culture collection (ATCC), 12301 Parklawn Drive, Rockville, Md. 20852, on Aug. 25, 1988, and has there been identified as follows:

Cl: Accession No.: HB 9803

The Cl antibody is of the IgG1 subclass. The antibody displays a very strong reactivity with tumor cells, particularly cells from colon and lung carcinomas. The Cl antibody shows no detectable binding to the lymphoma cell lines, CEM, MOLT-4, the B cell lymphoma line P3HR-1, and to melanoma cells.

In addition, the antibody of this invention does not display any immunohistologically detectable binding to normal human tissues such as fibroblasts, endothelial cells or epithelial cells from the major organs, e.g., kidney, spleen, liver, skin, lung, breast, colon, brain, thyroid, heart, lymph nodes or ovary. Nor does the antibody react with peripheral blood leukocytes. Thus, this antibody is superior to most known antitumor antibodies in its specificity for a range of tumor cells and in its high degree of specificity for tumor cells as compared to normal cells (See, e.g., Hellstrom et al., *Covalently Modified Antigens And Antibodies In Diagnosis And Therapy*, Quash/Rodwell (eds.), pp 24-28 (Marcel Dekker, Inc. (1989); and Bagshawe, *Br. J. Cancer*, 48:167-75 (1983)).

It should be understood that the present invention encompasses the Cl antibody described above and any fragments thereof containing the active binding region of the antibody, such as Fab, F(ab)$_2$ and Fv fragments. Such fragments can be produced from the Cl antibody using techniques well established in the art (see, e.g., Rousseaux et al., in *Methods Enzymol.*, 121:663-69, Academic Press (1986)).

In addition, the present invention encompasses antibodies that are capable of binding to the same antigenic determinant as the Cl antibody and competing with the Cl antibody for binding at that site. These include antibodies having the same antigenic specificity as the Cl antibody but differing in species origin, isotype, binding affinity or biological functions (e.g., cytotoxicity). For example, class, isotype and other variants of the antibody of the invention may be constructed using recombinant class-switching and fusion techniques known in the art (see, e.g., Thammana et al., *Eur. J. Immunol.*, 13:614 (1983); Spira et al., *J. Immunol. Meth.*, 74:307-15 (1984); Neuberger et al., *Nature*, 312:604-08 (1984); and Oi et al., supra)). Thus, chimeric antibodies or other recombinant antibodies (e.g., antibody fused to a second protein such as a lymphokine) having the same binding specificity as the Cl antibody fall within the scope of this invention. Furthermore, since the Cl antigen to which the antibody of the invention binds is a novel tumor antigen, the antibody of the invention includes antibodies that bind to any antigenic determinant on that Cl antigen, including determinants other than that with which the Cl antibody reacts.

Also included within the scope of the invention are anti-idiotypic antibodies of the Cl antibody of the invention. These anti-idiotypic antibodies can be produced using the Cl antibody as immunogen and are useful for diagnostic purposes in detecting humoral response to tumors and in therapeutic applications, e.g., in a vaccine, to induce an anti-tumor response in patients (See, e.g., Nepom et al., *Cancer And Metastasis Reviews*, 6:487-501 (1987); and Lee et al., *Proc. Nat'l. Acad. Sci. (USA)*, 82:6286-90 (1985)).

The Cl antibody can be used to isolate and characterize the Cl antigen to which it binds. Thus, Cl can be used as a probe to identify and characterize the epitope recognized by the antibody and to further define the Cl antigen on the surface of the carcinoma cells (see, e.g., Hakomori, *Ann. Rev. Immunol.*, 2:103-26 (1984); Brown et al., *J. Immunol.*, 127: 539-546 (1981); Brown et al., *Nature*, 296: 171-173 (1982); and Rose et al.; *Proc. Nat'l. Acad. Sci. (USA)*, 83: 1261-1265 (1986)).

The Cl antigen recognized by the monoclonal antibodies of the present invention comprises a novel cell surface glycoprotein antigen characteristic of tumor cells, particularly cells from carcinomas of the colon and lung. Cl antigen has a molecular weight of about 66,000 daltons when subjected to immunoprecipitation on polyacrylamide gel electrophoresis.

The amino terminal amino acid sequence of the novel Cl glycoprotein antigen is as follows:

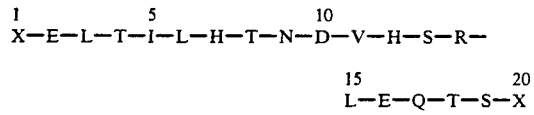

in which X represents an amino acid that has not been identified as yet, and the rest of the letters represent the conventional single letter abbreviations for amino acids. A comparison of the 20 residue Cl amino-terminal sequence with those stored in the current protein data base (PIR Release 16, March 1988; Gen BANK Release 57.0, September 1988; NEW, Nov. 30, 1988; DIF, Nov. 30, 1988; SWISSPROT, Nov. 30, 1988; LOSPRO, Nov. 30, 1988) reveals no significant sequence homology with any other known sequences.

The monoclonal antibody of the invention is also useful for diagnostic applications, both in vitro and in vivo, for the detection of human carcinomas carrying the Cl antigen with which the Cl antibody is specifically reactive. In vitro diagnostic methods are well known in the art (See, e.g., Roth, supra, and Kupchik, supra) and include immunohistological detection of tumor cells (e.g., on human tissue, cells or excised tumor specimens) or serologic detection of tumor-associated antigens (e.g., in blood samples or other biological fluids).

Immunohistological techniques involve contacting a biological specimen such as a tumor tissue specimen with the antibody of the invention and then detecting the presence on the specimen of the antibody complexed to its antigen. The formation of such antibody-antigen complexes with the specimen indicates the presence of tumor cells in the tissue. Detection of the antibody on the specimen can be accomplished using techniques known in the art, such as the immunoperoxidase staining technique, the avidin-biotin (ABC) technique or immunofluorescence techniques (see, e.g., Ciocca et al., *Meth. Enzymol.*, 121:562-79 (1986); Hellstrom et al., *Cancer Research*, 46:3917-23 (1986); and Kimball (ed.), *Introduction To Immunology* (2nd Ed.), pp. 113-117, Macmillan Publ. Co. (1986)). For example, immunoperoxidase staining was used as described in Example III, infra, to demonstrate the reactivity of the Cl antibody with lung and colon carcinomas, and the lack of reactivity of the antibody with normal human tissue specimens.

Serologic diagnostic techniques involve the detection and quantitation of tumor-associated antigens that have been secreted or "shed" into the serum or other biological fluids of patients thought to be suffering from carcinoma. Such antigens can be detected in the body fluids using techniques known in the art such as radioimmunoassays (RIA) or enzyme-linked immunosorbent assays (ELISA) wherein an antibody reactive with the "shed" antigen is used to detect the presence of the antigen in a fluid sample (see, e.g., Uotila et al., *J. Immunol. Methods*, 42:11 (1981) and Allum et al., supra, at pp. 48-51). These assays, using the Cl antibody disclosed herein, therefore can be used for the detection in biological fluids of the Cl antigen with which the Cl antibody reacts and thus the detection of various carcinomas in human patients. Thus, it is apparent from the foregoing that the Cl antibody of the invention can be used in most assays involving antigen-antibody reactions. These assays include, but are not limited to, standard RIA techniques, both liquid and solid phase, as well as ELISA assays, immunofluorescence techniques, and other immunocytochemical assays (see, e.g., Sikora et al. (eds.), *Monoclonal Antibodies*, pp. 32-52, Blackwell Scientific Publications, (1984)).

The Cl antibody of the invention is also useful for in vivo diagnostic applications for the detection of human tumors. One such approach involves the detection of tumors in vivo by tumor imaging techniques using the antibody labeled with an appropriate imaging reagent that produces detectable signal. Imaging reagents and procedures for labeling antibodies with such reagents are well known (see, e.g., Wensel and Meares, *Radio Immunoimaging and Radioimmunotherapy*, Esevier, N.Y. (1983); Colcher et al., *Meth. Enzymol.*, 121:802-16 (1986)). The labeled antibody may be detected by a technique such as radionuclear scanning (see, e.g., Bradwell et al. in *Monoclonal Antibodies for Cancer Detection and Therapy*, Baldwin et al. (eds.), pp. 65-85, Academic Press (1985)).

The Cl antibody of the invention has a number of in vivo therapeutic applications. In addition to being used alone to target tumor cells, the antibody can be used in conjunction with an appropriate therapeutic agent to treat human cancer. For example, the antibody can be conjugated or linked to a therapeutic drug or toxin for delivery of the therapeutic agent to the site of the cancer. Techniques for conjugating such therapeutic agents to antibodies are well known (see, e.g., Arnon et al., *Monoclonal Antibodies And Cancer Therapy*, Reisfeld et al. (eds.), pp. 243-56, Alan R. Liss, Inc., (1985); Hellstrom et al. in *Controlled Drug Delivery* (2nd ed.), Robinson et al. (eds.), pp. 623-53, Marcel Dekker, Inc., (1987); Thorpe, *Monoclonal Antibodies '84: Biological And Clinical Applications*, Pinchera et al. (eds.), pp. 475-506 (1985); and Thorpe et al., *Immunol. Rev.*, 62:119-58 (1982)). Since the Cl antibody is not easily internalized when cells are exposed to it in vitro, it may be preferable to target chemotherapeutic drugs to the tumor cells by coupling the antibody with an enzyme, e.g., using direct chemical coupling or recombinant DNA techniques. When such conjugates are localized to the tumor, the enzyme can convert an inactive (nontoxic) prodrug, which is administered after the conjugates have bound to the tumor cells, to an active anticancer drug. (See, e.g., Senter et al., *Proc. Nat'l. Acad. Sci. (USA)*, 85:4842-46 (1988)).

Alternatively, the antibody can be coupled to a source of high-energy radiation, e.g., a radioisotope such as $^{131}$I, which, when localized at the tumor site, results in a killing of several cell diameters (See, e.g., Order, in *Monoclonal Antibodies For Cancer Detection And Therapy*, Baldwin et al. (eds.), pp. 303-16, Academic Press, (1985)). According to yet another embodiment, the Cl antibody can be conjugated to a second antibody to form an antibody heteroconjugate for the treatment of tumor cells as described by Segal in U.S. Pat. No. 4,676,980.

Still other therapeutic applications for the Cl antibody of the invention include its use, either in the presence of complement or as part of an antibody-drug or antibody-toxin conjugate, to remove tumor cells from the bone marrow of cancer patients. According to this approach, autologous bone marrow may be purged ex vivo by treatment with the antibody and the marrow infused back into the patient (See, e.g., Ramsay et al., *J. Clin. Immunol.*, 8(2):81-88 (1988)).

Furthermore, chimeric or other recombinant Cl antibodies of the invention, as described earlier, may be used therapeutically. For example, a fusion protein comprising at least the antigen-binding region of the Cl antibody joined to at least a functionally active portion of a second protein having anti-tumor activity, e.g., a lymphokine or oncostatin, may be used to treat human tumors in vivo. In addition, a chimeric Cl antibody wherein the antigen-binding region of Cl is joined to a human Fc region, e.g., IgG1, may be used to promote antibody-dependent cellular cytotoxicity or complement mediated cytotoxicity. Furthermore, recombinant techniques known in the art can be used to construct bispecific antibodies wherein one of the binding specificities of the antibody is that of the Cl antibody (See, e.g., U.S. Pat. No. 4,474,893).

Finally, anti-idiotypic antibodies of the Cl antibody may be used therapeutically in active tumor immunization and tumor therapy (See, e.g., Hellstrom et al., "Immunological Approaches To Tumor Therapy Monoclonal Antibodies, Tumor Vaccines, And Anti-Idiotypes" in *Covalently Modified Antigens and Antibodies In Diagnosis and Therapy*, supra, at pp. 35-41).

It is apparent, therefore, that the present invention encompasses pharmaceutical compositions, combinations and methods for treating human tumors. For example, the invention includes pharmaceutical compositions for use in the treatment of human tumors comprising a pharmaceutically effective amount of a Cl antibody and a pharmaceutically acceptable carrier. The compositions may contain the Cl antibody, either unmodified, conjugated to a therapeutic agent (e.g., drug, toxin, enzyme or second antibody) or in a recombinant form (e.g., chimeric or bispecific Cl). The compositions may additionally include other antibodies or conjugates for treating carcinomas (e.g., an antibody cocktail).

The antibody compositions of the invention can be administered using conventional modes of administration, including, but not limited to, intravenous, intraperitoneal, oral; intralymphatic or administration directly into the tumor. Intravenous administration is preferred.

The antibody compositions of the invention may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The antibody compositions also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the compositions of this invention depends upon the severity and course of the disease, the patient's health and response to treatment, and the judgment of the treating physician. Accordingly, the dosages of the compositions should be titrated to the individual patient. Nevertheless, an effective dose of the antibody compositions of this invention may be in the range of from about 1 to about 5000 mg/m$^2$.

The novel antigen of the present invention, referred to as antigen Cl may also be used for therapeutic applications. The antigen can be purified from tumors or produced by recombinant DNA technology (Brown et al., copending U.S. patent application Ser. No. 827,313, filed on Feb. 7, 1986, incorporated by reference herein). The gene coding for the Cl antigen may be cloned by methods which first enrich the mRNA of the Cl antigen. By one such method, polysomes (consisting of mRNA ribosomes and nascent polypeptide chains) can be purified by immunoaffinity chromatography with antibody that recognizes the Cl antigenic determinant on the nascent chain. The mRNA is isolated by immunoprecipitation with, e.g., Cl antibody and the cDNA is cloned in an appropriate expression vector. Alternatively, Cl antibody or antiserum to Cl antigen might be used to screen a cDNA library using an expression vector. The purified or cloned Cl antigen may be administered alone as an immunogen or together with a proper immunological adjuvant.

Purified or cloned Cl antigen may be used in the methods of the invention as a vaccine to immunize against certain tumors. Procedures for preparing such vaccines are known in the art (see, e.g., Estin et al., *Proc. Nat'l. Acad. Sci. (USA)*, 85:1052 (1988)). Briefly, recombinant viruses are constructed for expression of the cloned tumor-associated antigen, for example, Cl antigen. Cells infected with the recombinant viruses will express the tumor antigen at the surface of the cells together with the host's incompatibility antigens and immunogenic viral proteins. This favors the induction of cellular immunity which plays a key role in tumor rejection. A suitable virus, for example, vaccinia virus derived from a plaque-purified virus of the Wyeth smallpox vaccine (New York City Board of Health strain), is used to construct a recombinant virus containing the coding sequence of the Cl antigen under control of the vaccinia virus "7.5 K" promoter (Hu et al., *J. Virol.*, 62:176-180 (1988)). The recombinant virus may then be administered intravenously as a vaccine to protect against cancer.

In order that the invention described herein may be more fully understood, the following examples are set forth. It should be understood that these examples are

EXAMPLE I

Preparation of the C1 Monoclonal Antibody

The C1 monoclonal antibody of the invention was produced using hybridoma fusion techniques described previously by Yeh et al., *Proc. Nat'l Acad. Sci. (USA)* (1979), supra. All cell lines used in the following examples were developed at Oncogen, Seattle, Wash., from samples of tumors obtained from humans either as solid tumors or effusions. Briefly, a three month-old BALB/c mouse was immunized four times using a membrane preparation of a human adenocarcinoma of the colon, designated H3059, and three times using cells from colon carcinoma cell line 3347. The membrane preparation was prepared as follows: Tumor was obtained from ascites effusion. 10 mls of lysing buffer (19.8 ml deionized water and 0.1 ml of 0.2M $NaHCO_3$ and 0.1 ml of 0.2M PMSF (protease inhibitor) in ethanol) was added to the cells and disrupted on ice 25 to 50 times. The mixture was then transferred to a 15 ml tube, and spun for 2 min. at $2000 \times G$ at $0°$ C. The supernatant was removed and transferred to a 5 ml cellulose tube. The pellet was checked under a microscope for lysis. The supernatant was then centrifuged on an ultracentrifuge for 15 min. at $37,000 \times G$ at $4°$ C. The supernatant was then aspirated and the pellet resuspended in at least 1 ml of PBS. The suspension was transferred to a 5 ml tube and sonicated on ice for 1 min. A 1:100 dilution was made and the protein concentration was determined using the Bradford procedure (Bradford, *Analytic Biochemistry*, 72:248-254 (1976)). The membrane preparations were stored frozen in aliquots of 0.2 ml in a Revco freezer ($-70°$ C.).

The mouse received seven (7) injections (inj.) as follows:

1st inj.: 100 µg membrane preparation + 100 µg muramyl dipeptide (MDP)/50 µl + 50 µl incomplete Freund's adjuvant given subcutaneously (s.c.) at 4 sites;

2nd inj.: 100 µg membrane preparation given s.c. at 4 sites;

3rd inj.: 100 µg membranes given intraperitoneally (i.p.);

4th inj.: 100 µg membranes given i.p. and s.c. at 4 sites;

5th inj.: $10^7$ 3347 cells given i.p. and s.c. at 4 sites;

6th inj.: $10^7$ 3347 cells given i.p. and s.c. at 4 sites;

7th inj.: $10^6$ 3347 cells given i.p. and s.c. at 4 sites;

Three days after the last immunization, the spleen was removed, and the spleen cells were suspended in culture medium. The spleen cells were then fused with ATCC CRL 1580, P3 X 63 - Ag8.653 cells, using polyethylene glycol (PEG), and the cell suspension grown in microliter wells in selective HAT medium as described by Yeh et al., *Proc. Nat'l. Acad Sci. (USA)*, supra. The mixture was seeded to form low density cultures originating from single fused cells or clones.

Binding Assays

The supernatants from these hybridoma cultures were then screened for direct binding activity on the colon cancer cell line 3347, using an ELISA assay similar to that described by Douillard et al., *Meth. Enzymol.*, 92:168-74 (1983). According to this assay, the antigen (with which the antibody being screened for is reactive) is immobilized on microtiter plates and then incubated with hybridoma supernatants. If a supernatant contains the desired antibody, the antibody will bind to the immobilized antigen and is detected by addition of an anti-immunoglobulin antibody-enzyme conjugate and a substrate for the enzyme which leads to a measurable change in optical density.

For this example, colon cancer cells were dispensed into a 96-well tissue culture plate (Costar, Cambridge, Mass.) and incubated overnight in a humid $37°$ C. incubator (5% $CO_2$). The cells were then fixed with 100 µl of freshly prepared 1.0% glutaraldehyde to a final well concentration of 0.5% and incubated for 15 min. at room temperature, followed by washing three times with $1 \times$ PBS. The cells were next blocked for 1 hr. with 5% BSA in PBS and washed again three times with PBS. The supernatants from the hybridoma cultures were then added at 100 µl/well, the wells incubated for 1 hr. at room temperature, and the cells washed three times with PBS. Next, goat anti-mouse horseradish peroxidase (Zymed, Calif.) diluted in 0.1% BSA and PBS was added to a concentration of 100 µl/well. The reaction mixture was incubated for either 1 hr. at room temperature or 30 min at $37°$ C. and the cells were then washed three times with PBS. o-phenylenediamine (OPD) was then added at 100 µl/well and the plates incubated in the dark at room temperature for 5-45 min. Antibody binding to the cells was detected by a color change in the wells that occurred within 10-20 min. The reaction was stopped by adding 100 µl/well $H_2SO_4$ and the absorbance read in a Dynatech (Alexandria, Va.) Microelisa autoreader at 492 nm.

Next the antibody was tested in a fluorescent assay using 3347 cells attached to coverslips and stained with fluorescein. Cultured 3347 cells were plated in 24 well tissue culture plates with sterile glass coverslips at a density of 1 to $2 \times 10^5$ cells per well and allowed to grow to 75-90% confluency. The cells were fixed with 3% paraformaldehyde for five minutes and then washed with binding buffer. 250 µl of antibody containing supernatant diluted 1:2 with binding buffer was added to each well and incubated for 30 min. at room temperature or at $37°$ C. The cells were then washed three times. Then 250 µl of an optimal dilution of FITC conjugated goat anti-mouse IgG antibody (TAGO, Burlingame, Calif.) was added to each well and incubated as before. The wash step was then repeated and the coverslips removed and mounted on microscope slides. Staining patterns were read using a fluorescence microscope.

Supernatants from wells positive on the colon carcinoma cell line in both the ELISA and fluorescence assays were further tested by immunohistology technology on 3347 cell pellets, colon carcinoma tissue and normal kidney, liver, and spleen tissues as described in Example II, infra.

It should be noted that the ELISA assay can be performed using intact cells or purified soluble antigen or cellular extracts as the immobilized antigen. When soluble antigen or cell extracts were used as antigen, the antigen was initially plated at 50 µl well in PBS and the plates were incubated overnight at room temperature before beginning the assay. When using intact cells as antigen, they may be used fresh or after fixation. In either case, the cells were initially plated at $10^4$ cells at 100 µl/well in culture medium and incubated overnight or until confluency in a $37°$ C. incubator (5% $CO_2$).

Hybridomas which produced antibodies binding to the colon cancer cell line and not to the normal tissues were thus selected, cloned, expanded in vitro, and further tested for antibody specificity. Those hybridomas which produced antibody reactive with human colon cancer were recloned, expanded, and injected into pristane-primed 3-month old BALB/c mice, where they grew as ascites tumors.

Following this procedure, hybridoma cell line Cl was obtained, cloned and injected into mice to develop as an ascites tumor. As disclosed above, the Cl hybridoma has been deposited with the ATCC. Antibody secreted into the ascites was purified on protein A- or protein G-Sepharose (see, e.g., Ey et al., *Immunochemistry*, 15:429-436 (1978)) or by gel filtration on Sephacryl S-300. Purified Cl antibody was used for further characterization.

EXAMPLE II

Characterization of The Cl Monoclonal Antibody

Isotype Determination

To determine the class of immunoglobulin produced by the Cl hybridoma, the following techniques were utilized:

a) Ouchterlony immunodiffusion

An aliquot of supernatant of the Cl hybridoma cells was placed into the center well of a 25% agar plate. Monospecific rabbit anti-mouse Ig isotypes antibodies (Southern Biotechnology, Birmingham, Ala.) were placed in the outer wells, and the plate was incubated for 24-48 hr. at 37° C. Precipitation lines were then read.

b) ELISA isotyping

Dynatech Immulon 96-well plates were coated with goat anti-mouse Ig antibodies at 1 µg/ml concentration, 50 µl/well in PBS and left covered overnight at 4° C. The plates were washed with PBS/Tween 20, 0.05%. After washing the plates, supernatants from the Cl hybridoma were added and incubated at room temperature for 1 hr. After washing with PBS/Tween 20 containing bovine serum albumin (BSA), plates were incubated at 37° C. for 2 hr. with monospecific goat anti-mouse Ig-HRP isotype antibodies coupled to peroxidase (Zymed). After washing, plates were incubated with 1 mg/ml o-phenylenediamine and 0.03% $H_2O_2$ in 0.1M citrate buffer, pH 4.5. Optical density at 490 and 630 nm was determined on a Dynatec ELISA plate reader.

Based on these procedures, it was determined that the Cl monoclonal antibody is of the IgG1 isotype.

Binding Characteristics of The Cl Monoclonal Antibody

The subcellular localization of antigen was determined by measuring antibody binding to cells before or after permeabilization with nonionic detergent. Antibodies binding to the cell surface of intact cultured cells were identified by direct fluorescence using the fluorescence activated cell sorter (FACS), as described by Hellstrom et al., *Cancer Research*, 46:3817-3923 (1986). Briefly, for binding analyses using a FACS cell sorter, $1 \times 10^6$ cultured cells were aliquoted in 15% fetal bovine serum (FBS) in IMDM media (Gibco, Grand Island, N.Y.) to a total volume of 500 µl tube. The cells were centrifuged for 1.5 min on a Serofuge and the supernatant removed. 100 µl of the Cl monoclonal antibody at 10 µg/ml and labeled with phycoerythrin was added to each tube, the contents of which was then mixed and incubated on ice for 30 min. The reaction mixture was washed three times with 1 ml of 15% FBS/IMDM by centrifugation for 1.5 min. on the Serofuge (tubes were blotted after the third wash). Each pellet was resuspended in 500 µl of PBS. Each sample was run on a Coulter Epics C FACS and the mean fluorescence intensity (MFI) was determined. From the MFI, the linear fluorescence equivalent (LFE) was determined. The LFE of each test sample divided by the LFE of a negative control gave a ratio between the brightness of cells stained by specific vs. control antibody (1.0 = no difference in fluoresence, 2.0 = fluoresence twice as bright, etc.). The binding data is shown in Table 1 below. Phycoerythrin was used as a fluorescent conjugate when attempts to conjugate Cl antibody with FITC were unsuccessful.

TABLE 1

| Binding of Cl Antibody to Various Cell Lines | |
|---|---|
| Cell Lines | Cl Antibody Binding Ratio |
| RCA Colon carcinoma (ca.) | 2.6 |
| 3347 Colon ca. | 76.0 |
| 2964 Lung ca. | 14.1 |
| 2981 Lung ca. | 12.4 |
| 3606 Lung ca. | 2.4 |
| 3464 Breast ca. | 2.8 |
| 3620 Melanoma | 1.0 |
| 2669 Melanoma | 7.4 |
| 3614 Melanoma | 3.7 |
| Peripheral blood cells | 1.0 |
| CEM T lymphocytes | 1.0 |
| Molt-4 T lymphocytes | 1.0 |
| P3yHR-1 B lymphoma | 1.1 |

As Table 1 demonstrates, the Cl monoclonal antibody reacted with lung and colon carcinoma cell lines, but did not react with T or B lymphoma lines nor with normal peripheral blood leukocytes. Weak reactivity with 2 of 3 melanoma lines was also observed.

Immunohistology

The PAP technique of L. A. Sternberger as described in *Immunochemistry*, pp. 104-69, John Wiley & Sons, New York (1979), as modified by Garrigues et al., *Int. J. Cancer*, 29:511-15 (1982), was used for immunohistological studies on frozen tissue sections. The target tissues for these tests were obtained at surgery and frozen within 4 hr. of removal using isopentane precooled in liquid nitrogen. Tissues were then stored in liquid nitrogen or at −70° C. until used. Frozen sections were prepared, air-dried, treated with acetone and dried again (see Garrigues et al., supra). Sections to be used for histologic evaluation were stained with hematoxylin. To decrease non-specific backgrounds, sections were preincubated with normal human serum diluted 1/5 in PBS (see Garrigues et al., supra). Mouse antibodies, rabbit anti-mouse IgG, and mouse PAP were diluted in a solution of 10% normal human serum and 3% rabbit serum. Rabbit anti-mouse IgG (Sternberger-Meyer Immunochemicals, Inc., Jarettsville, Md.) was used at a dilution of 1/50. Mouse peroxidase-antiperoxidase complexes (PAP, Sternberger-Meyer Immunochemicals, Inc.) containing 2 mg/ml of specifically purified PAP were used at a dilution of 1/80.

The staining procedure consisted of treating serial sections with either specific antibody, i.e., Cl, or a control antibody for 2.5 hr., incubating the sections for 30 min. at room temperature with rabbit anti-mouse IgG diluted 1/50 and then exposing the sections to mouse PAP complexes diluted 1/80 for 30 min. at room temperature. After each treatment with antibody, the slides were washed twice in PBS.

The immunohistochemical reaction was developed by adding freshly prepared 0.5% 3,3'-diaminobenzidine tetrahydrochloride (Sigma Chemical Co., St. Louis, Mo.) and 0.01% $H_2O_2$ in 0.05M Tris buffer, pH 7.6, for 8 min. (see Hellstrom et al., J. Immunol., 127:57-60 (1981)). Further exposure to a 1% $OsO_4$ solution in distilled water for 20 min. intensified the stain. The sections were rinsed with water, dehydrated in alcohol, cleared in xylene, and mounted on slides. Parallel sections were stained with hematoxylin.

The slides were each evaluated under code and coded samples were checked by an independent investigator. Typical slides were photographed by using differential interference contrast optics (Zeiss-Nomarski). The degree of antibody staining was evaluated as 0 (no reactivity), + (a few weakly positive cells), + + (at least one third of the cells positive), + + + (most cells positive), + + + + (all cells strongly positive). Because differences between + and 0 staining were less clear cut than between + and + + staining, a staining graded as + + or greater was considered "positive." Both neoplastic and stroma cells were observed in tumor samples. The staining recorded is that of the tumor cells because the stroma cells were not stained at all or were stained much more weakly than the tumor cells.

Table 2 below presents the immunohistological staining of various tumor and normal tissue specimens using the Cl monoclonal antibody. As the table clearly demonstrates, the Cl antibody reacts with human colon and lung carcinomas but not detectably with cells from breast carcinoma or melanoma; the only ovarian carcinoma sample tested was positive. The Cl antibody shows no reactivity with any of the number of normal human tissues tested.

TABLE 2

Immunoperoxidase Staining of Tumors and Normal Tissue Specimens with Cl Monoclonal Antibody

| Tissue Type | Antibody Binding (Number of Positive Tumors/ Total Number of Tumors Tested) |
|---|---|
| Colon carcinoma (ca.) | 9/9 |
| Lung ca. | 12/17 |
| Breast ca. | 0/14 |
| Ovarian ca. | 1/1 |
| Melanoma | 0/6 |
| Sarcoma | 1/5 |
| Normal Tissues: | |
| SPLEEN | 0/4 |
| KIDNEY | 0/5 |
| LIVER | 0/3 |
| HEART | 0/2 |
| OVARY | 0/1 |
| ADRENAL | 0/2 |
| TESTIS | 0/2 |
| BREAST | 0/2 |
| TONSIL | 0/1 |
| SKIN | 0/5 |
| LUNG | 0/5 |
| COLON | 0/7 |
| BRAIN | 0/2 |
| THYROID | 0/2 |
| LYMPH NODES | 0/3 |
| RETINA | 0/1 |
| PANCREAS | 0/2 |

EXAMPLE III

Cl Antigen Recognized By Cl Antibody Purification

Cl antigen was isolated from colon carcinoma 3347 cells, and from lung carcinoma 2964 cells and partially purified by immunoaffinity chromatography. Cl antigen was purified to homogeneity by SDS-PAGE and recovered from SDS-polyacrylamide gels by electroelution or electroblotting onto membranes.

Following electrophoresis, the SDS-polyacrylamide gel was stained with Coomassie Brilliant Blue and destained. The stained Cl antigen band (Mr=66,000) was excised with a razor blade and subjected to electroelution.

Cl antigen was also recovered from SDS-polyacrylamide gels by electroblotting onto Immobilon membrane (Millipore Corp., Bedford, Mass.) using Mini-Transblot Electrophoretic Transfer Cell (BioRad Laboratories, Richmond, Calif.), as described by Matsudaira in J. Biol. Chem., 261:10035-10038 (1987). The membrane was stained with Coomassie Brilliant Blue, destained, and the stained Cl antigen band (Mr=66,000) was excised with a razor blade for subsequent aminoterminal sequence analysis.

Sequence Analysis

Automated Edman degradation was performed on three preparations of Cl antigen with 33 pmol of antigen from 3347 cells, 49 pmol of antigen from 2964 cells, and 6 pmol of antigen from 2964 cells.

The aminoterminal sequence of Cl antigen was as follows:

$$\begin{array}{cccccccccccccc} 1 & & & & 5 & & & & & 10 & & & & \\ X-E-L-T-I-L-H-T-N-D-V-H-S-R- \\ & & & & & & & & & & & 15 & & 20 \\ & & & & & & & & & & & L-E-Q-T-S-X \end{array}$$

The aminoterminal sequence of Cl antigen was compared against the following data bases:

| | | Number of Sequences |
|---|---|---|
| 1. PIR | (Release 18.0, Sept. 1988) | 8,588 |
| 2. GenBANK | (Release 57.0, Sept. 1988) | 19,044 |
| 3. NEW | (November 30, 1988) | 4,148 |
| 4. DIF | (November 30, 1988) | 2,610 |
| 5. SWISSPROT | (November 30, 1988) | 7,724 |
| 6. LOSPRO | (November 30, 1988) | 11,343 |

The sequence comparison did not reveal significant matches with any other known sequence.

Immunological Characterization Western Blot Analysis

Immunoaffinity-purified Cl antigen was subjected to SDS-PAGE (10% acrylamide) and electroblotted onto nitrocellulose membrane (Schleicher and Schuell, Keene, N.H.), as described by Towbin et al. in Proc. Nat'l. Acad. Sci. (USA), 76:4350-4354 (1979). Cl antigen was immunodetected using alkaline phosphatase-conjugated rabbit anti-mouse IgG as a second antibody (ICN Biomedicals, Lisle, Ill.) and 5-bromo-4-chloro-3-indolyl phosphate p-toluidine salt and p-nitro blue tetrazolium chloride as chromogens (BioRad Labgratories). Immunodetection revealed that the major band at Mr=66,000 was specifically stained with Cl antibody.

Radioimmunoprecipitation 3347 cells were metabolically labeled with $^3$H-glucosamine by incubation in RPMI 1640 medium (glucose-free RPMI 1640) supplemented with 10% dialyzed fetal bovine serum for 4 hr. at 37° C. The cell pellet was extracted with 20 mM Tris-HCl buffer, pH 7.5, 100 mM NaCl, 1 mM EDTA, 0.5% NP-40, PMSF (10 μg/ml) aprotinin (10 μg/ml). Cl antigen was immunoprecipitated by incubating the cell lysate with Cl antibody for 1 hr. at 4° C. The antigen-antibody complex was precipitated with goat anti-mouse IgG and Pansorbin (Calbiochem, San Diego, Calif.). The washed immunoprecipitate was analyzed by SDS-PAGE under reducing and non-reducing conditions and visualized by fluorography after impregnating the gel with EN$^3$-HANCE ™.

2964 cells, 2707 cells, CH$_3$T$_2$ cells, and 2981 cells, all derived from adenocarcinomas of the lung, were surface-labeled with $^{125}$I by the lactoperoxidase method described by Vitetta et al. in *J. Exp. Med.*, 134:242-264 (1971). Cl antigen was immunoprecipitated from $^{125}$I-labeled cell lysates with Cl antibody, goat anti-mouse IgG, and Pansorbin. The immunoprecipitates were analyzed by SDS-PAGE under reducing conditions and visualized by autoradiography.

Cl antibody specifically precipitated Cl antigen with a Mr of from about 66,000 to 68,000. These data demonstrate that the antigenic determinant recognized by Cl monoclonal antibody is localized on a unique single-chain glycoprotein with a Mr of about 66,000. The Cl antigen is associated with a variety of tumor cells, particularly lung and colon carcinoma tumors.

It is apparent that many modifications and variations of this invention as set forth above may be made without departing from the spirit and scope. The specific embodiments described are given by way of example only, and the invention is limited only by the terms of the appended claims.

What is claimed is:

1. A monoclonal antibody selected from the group consisting of the monoclonal antibody produced by hybridoma cell line ATCC No. HB 9803, which antibody binds to a determinant site on a cell surface glycoprotein antigen of human tumor cells, antibodies that are capable of binding to the same antigenic determinant as does the monoclonal antibody produced by hybridoma cell line ATCC No. HB 9803 and competing with the monoclonal antibody produced by ATCC No. HB 9803 for binding at that antigenic determinant, and binding fragments of the monoclonal antibody produced by ATCC No. HB 9803.

2. The monoclonal antibody of claim 1 wherein said tumor cells are carcinoma cells.

3. The monoclonal antibody of claim 2 wherein said carcinoma cells are selected from the group consisting of lung and colon carcinoma cells.

4. The monoclonal antibody of claim 1 conjugated to a label capable of producing a detectable signal.

5. The monoclonal antibody of claim 4 wherein the label is selected from the group consisting of a radionuclide, an enzyme, a fluorescent agent and a chromophore.

6. A monoclonal antibody produced by hybridoma cell line ATCC No. HB 9803, which antibody binds to a cell determinant site on a cell surface glycoprotein antigen of human tumor cells, said antigen characterized by a molecular weight of about 66,000 daltons, as determined by polyacrylamide gel electrophoresis, and having an amino terminal amino acid sequence as follows:

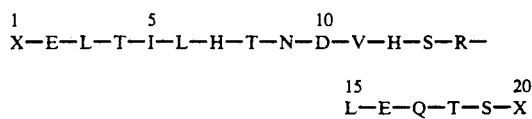

in which X represents an unidentified amino acid, and binding fragments of the monoclonal antibody.

7. A monoclonal antibody produced by a hybridoma cell line formed by fusion of a myeloma cell and a cell capable of producing antibody which binds to a determinant on a cell surface glycoprotein antigen of human tumor cells, said antigen having a molecular weight of about 66,000 daltons as determined by polyacrylamide gel electrophoresis, and having an amino terminal sequence as follows:

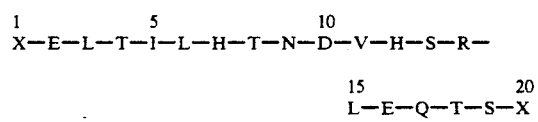

in which X represents an unidentified amino acid, and antibodies that are capable of binding to the same antigenic determinant as does the monoclonal antibody capable of binding to the glycoprotein antigen having a molecular weight of about 66,000 daltons and competing with the monoclonal antibody capable of binding to the glycoprotein antigen for binding at that antigenic determinant, and binding fragments of the monoclonal antibody capable of binding to the glycoprotein antigen.

8. The monoclonal antibody of claim 7 which is of class IgG.

9. The monoclonal antibody of claim 7 which is of subclass IgG1.

10. The monoclonal antibody of claim 7 which is a murine antibody.

11. A monoclonal antibody which binds a determinant site on a cell surface glycoprotein antigen associated with human tumor cells, said antigen characterized by a molecular weight of about 66,000 daltons as determined by polyacrylamide gel electrophoresis, and having an amino terminal amino acid sequence as follows:

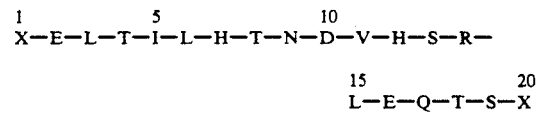

in which X represents an unidentified amino acid, and binding fragments of the monoclonal antibody.

12. The monoclonal antibody of claim 11 consisting of the monoclonal antibody produced by hybridoma cell line ATCC No. HB 9803.

13. The monoclonal antibody of claim 11 which is a human antibody.

14. The monoclonal antibody of claim 11 which is a mouse-human antibody.

15. An immunoassay for the detection of human tumors comprising:

a) combining a monoclonal antibody reactive with a cell surface glycoprotein antigen associated with human tumor cells, said antigen characterized by a molecular weight of about 66,000 daltons as determined by polyacrylamide gel electrophoresis and having an amino terminal amino acid sequence as follows:

```
1         5              10
X—E—L—T—I—L—H—T—N—D—V—H—S—R—
                      15          20
                      L—E—Q—T—S—X
``` in which X represents an unidentified amino acid, with a sample of tumor cells said antibody labeled so as to be capable of detection; and b) assaying for said labeled monoclonal antibody binding to tumor cells associated with said antigen.

16. The immunoassay of claim 15 wherein said monoclonal antibody is the antibody produced by hybridoma cell line ATCC No. HB 9803.

17. The immunoassay of claim 15 wherein said antibody is labelled with a label selected from the group consisting of a radionuclide, an enzyme, a fluorescent agent and a chromophore.

18. A method for detecting tumors which comprises: contacting the monoclonal antibody of claim 1, 6, 8, or 12 with a human tissue or fluid sample and detecting interaction of said antibody with any antigenically corresponding tumor cells or antigenic determinants thereof in said sample by observing a detectable signal produced by the interaction of said antibody with said tumor cells or antigenic determinants thereof.

19. The method of claim 18 wherein said tumor cells are lung carcinoma cells and the human tissue is lung tissue.

20. The method of claim 18 wherein said tumor cells are colon carcinoma cells and the human tissue is colon tissue.

21. The method of claim 18 wherein the interaction of said monoclonal antibody with said tumor cells is detected by immunohistological staining.

22. Hybridoma cell line ATCC No. HB 9803 monoclonal antibody capable of binding to a determinant on a cell surface glycoprotein antigen of human tumor cells.

23. Hybridoma cell line ATCC No. HB 9803 formed by fusing on ATCC CRL 1580, P3×63-Ag 8.653 mouse myeloma cell with a mouse splenocyte obtained from a BALB/c mouse immunized with colon adenocarcinoma H3059 cells which produces a monoclonal antibody which binds to a determinant of cell surface glycoprotein antigen of human tumor cells having a molecular weight of about 66,000 daltons and having an amino terminal amino acid sequence as follows:

```
1         5              10
X—E—L—T—I—L—H—T—N—D—V—H—S—R—
                      15          20
                      L—E—Q—T—S—X
``` in which X represents an unidentified amino acid as determined by polyacrylamide gel electrophoresis.

24. A continuous cell line which produces a monoclonal antibody which specifically binds a determinant site on a cell surface glycoprotein antigen associated with tumor cells, said antigen having a molecular weight of about 66,000 daltons and having an amino terminal amino acid sequence as follows:

```
1         5              10
X—E—L—T—I—L—H—T—N—D—V—H—S—R—
                      15          20
                      L—E—Q—T—S—X
``` in which X represents an unidentified amino acid, which comprises: a hybridoma of a lymphocyte capable of producing antibody against said antigen and a myeloma cell.

* * * * *